United States Patent [19]

Oude Alink

[11] Patent Number: 4,480,095
[45] Date of Patent: Oct. 30, 1984

[54] HEXAHYDROPYRIMIDINES AND CORRESPONDING LINEAR POLYAMINES

[75] Inventor: Bernardus A. Oude Alink, St. Louis, Mo.

[73] Assignee: Petrolite Corporation, St. Louis, Mo.

[21] Appl. No.: 970,413

[22] Filed: Dec. 18, 1978

[51] Int. Cl.³ ........................................ C07D 239/04
[52] U.S. Cl. .................................. 544/242; 424/251
[58] Field of Search ........................................ 544/242

[56] References Cited

U.S. PATENT DOCUMENTS

| | | | |
|---|---|---|---|
| 2,486,648 | 11/1949 | Haury | 260/585 |
| 2,525,855 | 10/1950 | Bergmann | 544/242 |
| 2,535,747 | 12/1950 | Morey | 260/251 |
| 2,675,390 | 4/1954 | Rosenblatt | 544/242 |
| 3,502,578 | 3/1970 | Raifsnider | 544/242 |
| 3,502,671 | 3/1970 | Hodge | 544/242 |
| 3,904,625 | 9/1975 | Alink | 544/242 |
| 4,085,104 | 4/1978 | Alink | 544/242 |
| 4,104,249 | 8/1978 | Alink | 544/242 |
| 4,145,545 | 3/1979 | Alink | 544/242 |

Primary Examiner—Nicholas S. Rizzo
Attorney, Agent, or Firm—Sidney B. Ring; Hyman F. Glass; Leon J. Bercovitz

[57] ABSTRACT

This invention relates to a process of reducing 2,4,5-trialkyl 2,3,4,5-tetrahydropyrimidine and/or 2,5,6,8,9-pentaalkyl 1,3,7-triazabicyclo (3,3,1) non-3-enes to yield 2,4,5-trialkylhexahydropyrimides and/or 2,4,5,6-tetraalkyl-5-(2-azoalkyl) hexahydropyrimidines; and to the cleavage of the above reduced products so as to convert the above hexahydropyrimides from cyclic amines to corresponding linear diamines and triamines. This invention also relates to the products produced by the processes.

11 Claims, No Drawings

HEXAHYDROPYRIMIDINES AND CORRESPONDING LINEAR POLYAMINES

In Patent Application Ser. No. 932,088 filed Aug. 8, 1978 there is described and claimed:

(1) The reaction of an aldehyde with ammonia to yield 2,4,6-trialkyl (or aralkyl)-1,3,5-hexahydrotriazines (Formula I) in accord with the equation

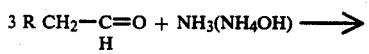

Formula I

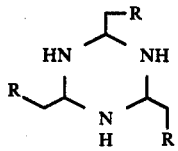

(2) The deammoniation of Formula I to yield N,N'-dialkylidene 1,1-diaminoalkane (Formula II) in accord with the equation

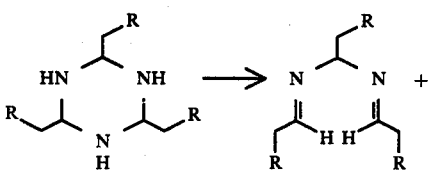

Formula II (3) The reaction of N,N'-dialkylidene 1,1-diaminoalkanes in the presence of a Lewis acid to form 2,5,6,8,9-penta-alkyl (or aralkyl)-substituted 1,3,7-triazabicyclo (3,3,1) non-3-enes's (TBN's), or mixtures thereof, according to the equation:

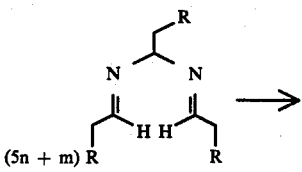

N,N'—dialkylidene 1,1-diaminoalkane

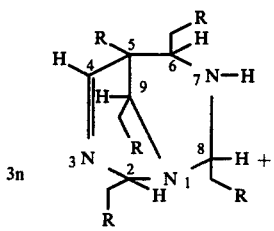

2,5,6,8,9-Penta alkyl (or aralkyl) substituted 1,3,7-triazabicyclo (3,3,1) non-3-ene (TBN)

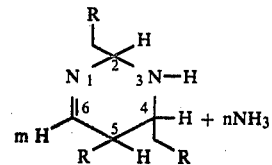

Formula IV 2,4,5-Trialkyl (or aralkyl) substituted tetrahydropyrimidine (THP)

In carrying out the above reactions it is not necessary to isolate the N,N'-dialkylidene 1,1-diamino alkane. The reaction can be carried out in one step by heating the 2,4,6-Trialkyl (or aralkyl) 1,3,5-hexahydrotriazine in the presence of a Lewis acid until conversion to the TBN and/or THP is effected.

The R Group: Any suitable aldehyde can be employed such as alkyl, etc., but preferably linear alkyl aldehydes. The reaction can also be effected with other aldehydes, preferably where a second methylene to the aldehyde group is present, i.e.,

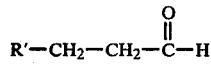

including aralkyl, etc., groups.

Thus, alkyl groups having from about 1 to 30 carbons such as from about 1-18 carbons, for example from about 1-12 carbons, but preferably lower alkyls having from about 1-8 carbons, can be employed.

I have now discovered that 2,4,5-trialkyl (or aralkyl) 2,3,4,5-tetrahydropyrimidines and/or 2,5,6,8,9-pentaalkyl-(or aralkyl)-1,3,7-triazabicyclo (3,3,1) non-3-enes can be reduced to yield 2,4,5-trialkyl (or aralkyl)-hexahydropyrimidines and/or 2,4,5,6-tetraalkyl-5-(2-azaalkyl) hexahydropyrimidines according to the following equation:

Formula III

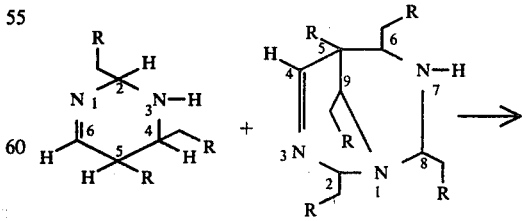

2,4,5-Trialkyl (or aralkyl)-2,3,4,5-tetrahydropyrimidine 2,5,6,8,9-Pentaalkyl (or aralkyl)-1,3,7-triazabicyclo (3,3,1) non-3-ene

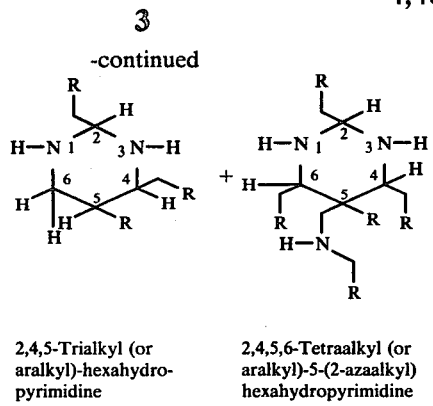

2,4,5-Trialkyl (or aralkyl)-hexahydro-pyrimidine 2,4,5,6-Tetraalkyl (or aralkyl)-5-(2-azaalkyl) hexahydropyrimidine Although reaction conditions such as time, temperature, solvent (if employed), etc., can vary widely, the preferred conditions will depend on various factors such as the particular reactants, the interrelationship of conditions, etc. Thus, any suitable reaction time, temperature, solvent, etc., can be employed provided the desired products are produced. Any suitable method of hydrogenation can be employed to produce the desired product. Thus, hydrogenation may be carried out with a reducing agent for example, sodium in ethanol, lithium aluminum hydride, lithium borohydride, magnesium-isopropanol, sodium trimethoxy borohydride, zinc, sodium borohydride, etc., or by hydrogenation with the use of a catalyst, for example platinum on carbon, Raney nickel, palladium on carbon, rhodium on carbon, etc.

I have also discovered that the substituted hexahydropyrimidines may be converted to the corresponding polyamines such as diamines and triamines respectively by treating the hexahydropyrimidines with aqueous acid under conditions capable of ring cleavage, for example by refluxing with aqueous mineral acids such as HCl sulfuric, etc., for a sufficient time to produce the cleaved products according to the following equation:

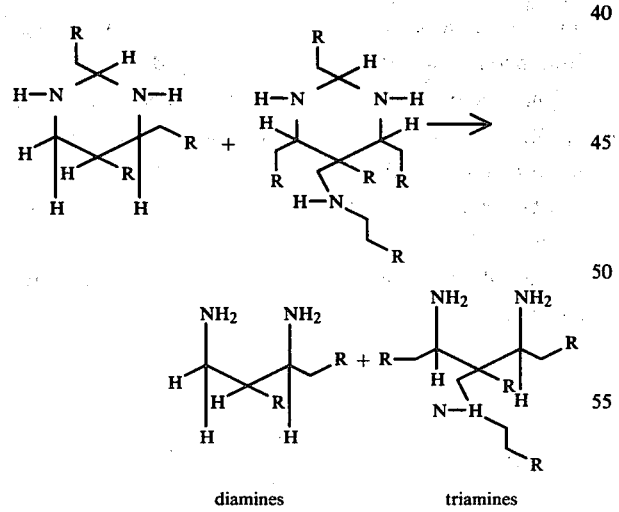

diamines        triamines

The following examples are presented for purposes of illustration and not of limitation.

EXAMPLE 1

5-(2-azapentyl)-5-methyl-2,4,6-triethylhexahydropyrimidine

A sample of 1330 cc. of 28% ammonium hydroxide was cooled to 2° C. Over a 2 hours period 290 grams of propionaldehyde was added while a reaction temperature of 0°-10° C. was maintained. After completion of the addition, the reaction mixture was stored at about 3° C. for 4 days and 400 grams of sodium chloride was added. The resulting product was extracted three times with ether and the ethereal solution after drying over anh. $MgSO_4$ evaporated under diminished pressure to yield 119 grams of 2,4,6-triethyl 1,3,5-hexahydrotriazine.

A mixture of 117 grams of 2,5,6-triethyl 1,3,5-hexahydrotriazine, 117 grams of hexanes, and 1.5 grams of ammonium chloride was refluxed under azeotropical conditions for 5 hours. The solution was filtered and evaporated under diminished pressure to yield 97 grams of 5-methyl-2,6,8,9-tetraethyl-1,3,7-triazabicyclo (3,3,1) non-3-ene.

To a mixture of 70 grams of 5-methyl-2,6,8,9-tetraethyl-1,3,7-triazabicyclo (3,3,1) non-3-ene, 0.5 grams of sodium hydroxide, and 190 grams of ethanol was added, with stirring, over a ½ hour period 9 grams of sodium borohydride. The mixture was stirred for 20 hours at ambient temperature. The ethanol was removed under diminished pressure and the resulting product was added to water and extracted with ether. The ethereal solution, after drying over anh. $MgSO_4$, was evaporated under diminished pressure to yield 64.2 grams of 5-(2-azapentyl)-5-methyl-2,4,6-triethylhexahydropyrimidine, b.p. 138°-150° C./20 torr.

EXAMPLE 2

7-Amino-6-(1-aminopropyl)-6-methyl-4-azanonane

A mixture of 21.1 grams of 5-(2-azapentyl)-5-methyl-2,4,6-triethylhexahydropyrimidine, prepared as described in example 1, 25 grams of conc. HCl and 25 grams of water was refluxed for 2 hours. The organic layer which separated was removed and discarded and the aqueous solution after extraction with ether was basified with a sodium hydroxide solution. The organic layer which separated was removed and the aqueous phase extracted with ether. The ethereal solution was combined with the organic layer and after drying evaporated under diminished pressure to yield 15.0 grams of 7-amino-6-(1-aminopropyl)-6-methyl-4-azanonane; b.p. 72°-76° C./0.05 torr; Infrared spectrum, 2.97 and 3.05μ (N-H) and 6.15μ ($NH_2$); $^1H$ nuclear magnetic resonance spectrum, solvent $CDCl_3$, internal reference tetramethylsilane, δ in ppm: 3.07-2.30, 6H; 2.00-1.14, 6H; 1.14-0.67, 12H. $^{13}C$ nuclear magnetic resonance spectrum, solvent $CDCl_3$, internal reference tetramethylsilane, δ in ppm:

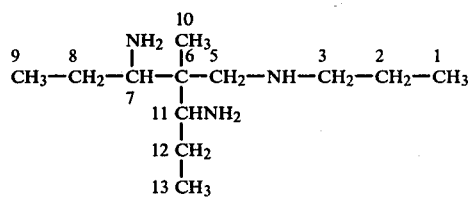

11.9(1); 23.2(2); 52.9 and 52.8(3); 54.7 and 54.3(5); 42.9 and 43.1(6); 58.8, 56.7 and 57.5(7,11); 24.9, 24.7 and 25.7(8,12); 12.2(9,13); 19.2 and 17.0(10).

Anal. Calculated for $C_{12}H_{29}N_3$: C, 66.98; H, 13.49; N, 19.54; Found: C, 67.11; H, 13.51; N, 19.41.

EXAMPLE 3

5-(2-azahexyl)-5-ethyl-2,4,6-tripropylhexahydropyrimidine and 2,4-dipropyl-5-ethylhexahydropyrimidine To a sample of 500 grams of 28% ammonium hydroxide was added at 25°-34° C. over a 1 hour period with stirring 242 grams of butyraldehyde. After the addition was completed the mixture was stirred for 1 hour at ambient temperature. The organic layer which separated was taken up in hexanes. The hexane solution after drying over sodium hydroxide was evaporated under diminished pressure to yield 206 grams of 2,4,6-tripropyl 1,3,5-hexahydrotriazine.

A mixture of 204 grams of 2,4,6-tripropyl 1,3,5-hexahydrotriazines, 250 grams of hexanes and 2 grams of acetic acid was refluxed for 5 hours. Ammonia gas was evolved during the reaction. After the reaction was completed, the hexanes were removed under diminished pressure to yield 188.6 grams of a mixture of 25% of 2,4-dipropyl-5-ethyl-2,3,4,5-tetrahydropyrimidine and 75% of 5-ethyl-2,6,8,9-tetrapropyl-1,3,7-triazabicyclo (3,3,1) non-3-ene.

A mixture of 141.0 grams of 25% of 2,4-dipropyl-5-ethyl-2,3,4,5-tetrahydropyrimidine and 75% of 5-ethyl-2,6,8,9-tetrapropyl-1,3,7-triazabicyclo (3,3,1) non-3-ene, 1 gram of sodium hydroxide and 377 grams of ethanol was treated with 16 grams of sodium borohydride over a 1 hour period. The resulting mixture was stirred for 19 hours at ambient temperature. The ethanol was removed under diminished pressure and the resulting product added to water. The organic layer which separated was removed and the aqueous layer was extracted with ether. The ethereal solution was combined with the organic layer to yield 135 grams of a mixture of 25% of 2,4-dipropyl 5-ethylhexahydropyrimidine and 75% of 5-(2-azahexyl)-5-ethyl-2,4,6-tripropylhexahydropyrimidine which were separated by fractional distillation. 2,4-Dipropyl 5-ethylhexahydropyrimidine, b.p. 56°-58° C./0.05 torr. Infrared spectrum, 3.05µ (N-H); $^{13}C$ nuclear magnetic resonance spectrum, solvent $CDCl_3$, internal reference tetramethylsilane, δ in ppm:

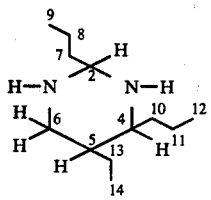

71.3(2); 59.9(4); 43.2(5); 50.9(6); 39.6(7); 18.6(8); 14.2(9); 35.9(10); 18.9(11); 14.4(12); 22.8(13); 11.1(14).

Anal. Calculated for $C_{12}H_{26}N_2$: C, 72.72; H, 13.13; N, 14.14; Found: C, 72.71; H, 13.19; N, 14.02.

5-(2-Azahexyl)-5-ethyl-2,4,6-tripropylhexahydropyrimidine, b.p. 121°-122° C./0.03 torr. Anal. Calculated for $C_{20}H_{43}N_3$: C, 73.85; H, 13.23; N, 12.92. Found: C, 74.46; H, 13.17; N, 13.12.

EXAMPLE 4

8-Amino-7-(1-aminobutyl)-7-ethyl-5-azaundecane and 4-Amino-3-(aminomethylene) heptane A sample of 64 grams of a mixture of 25% 2,4-dipropyl-5-ethylhexahydropyrimidine and 75% of 5-(2-azahexyl)-5-ethyl-2,4,6-tripropylhexahydropyrimidine, 64 grams of concentrated HCl and 64 grams of water were mixed and refluxed for 2 hours. The organic layer, 16.5 grams of a mixture of butyraldehyde and 2-ethyl-2-hexanol, which formed was separated. The aqueous acid solution was extracted with ether and basified with a sodium hydroxide solution, to yield an organic layer. The basic solution was extracted two times with ether and the ethereal extracts combined with the organic layer. The ethereal solution, after drying, was evaporated under diminished pressure to yield 48.5 grams of a mixture of 25% of 4-amino-5-(aminomethylene) heptane and 75% of 8-amino-7-81-aminobutyl)-7-ethyl-5-azaundecane. The mixture was separated by distillation. 4-Amino-3-(aminomethylene)heptane, b.p. 45° C./0.1 torr; $^{13}C$ nuclear magnetic resonance spectrum, solvent $CDCl_3$, internal reference tetramethylsilane, δ in ppm:

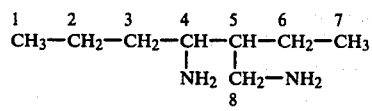

14.3(1); 20.0(2); 38.1(3); 52.3(4); 48.2(5); 21.7(6); 12.1(7); 41.6(8).

Anal. Calculated for $C_8H_{20}N_2$: C, 66.67; H, 13.89; N, 19.44; Found: C, 66.91; H, 13.80; N, 19.49.

8-Amino-7-(1-aminobutyl)-7-ethyl-5-azaundecane, b.p. 118°-125° C./0.05 torr; $^{13}C$ nuclear magentic resonance spectrum, solvent $CDCl_3$, internal reference tetramethylsilane, δ in ppm:

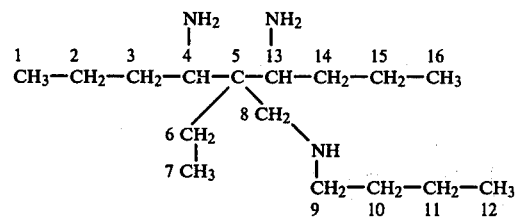

14.4(1,16); 20.7(2,15); 35.1, 35.4(3,14); 55.7, 54.7, 54.0(4,13); 44.2, 43.9(5); 26.7, 24.5(6); 9.6(7); 50.6(8); 55.1(9); 32.4(10); 21.1(11); 4.1(12).

Anal. Calculated for $C_{16}H_{37}N_3$: C, 70.85; H, 13.65; N, 15.50; Found: C, 70.38; H, 13.73; N, 15.52.

EXAMPLE 5

9-Amino-8(1-aminopentyl)-8-propyl-6-azatridecane and 5-Amino-4-(aminomethylene) nonane To a sample of 560 cc. of 28% ammonium hydroxide was added over a 1½ hours period 179 grams of valeraldehyde with stirring while a reaction temperature of 20°-42° C. was maintained. After the addition was completed, stirring was continued for 2 hours at ambient temperature. The organic layer which separated was taken up in hexanes and the hexane solution after drying over sodium hydroxide was evaporated under diminished pressure to yield 169.5 grams of 2,4,6-tributyl 1,3,5-hexahydrotriazine.

A mixture of 168.8 grams of 2,4,6-tributyl 1,3,5-hexahydrotriazine, 228 grams of hexanes and 1.5 grams of ammonium chloride were refluxed under azeotropical conditions for 19 hours. The solution was filtered and evaporated under diminished pressure to yield 157.5 grams of a mixture of 20% of 2,4-dibutyl-5-propyl-2,3,4,5-tetrahydropyrimidine and 80% of 5-propyl-2,6,8,9-tetrabutyl-1,3,7-triazabicyclo (3,3,1) non-3-ene.

To the mixture of 130 grams of 20% 2,4-dibutyl-5-propyl-2,3,4,5-tetrahydropyrimidine and 80% of 5-propyl-2,6,8,9-tetrabutyl-1,3,7-triazabicyclo (3,3,1) non-3-ene and 1 gram of sodium hydroxide in 375 grams of ethanol, was added over a ¾ hour period 17 grams of sodium borohydride. The mixture was stirred for 20 hours and the solvent removed under diminished pressure. The resulting product was added to water and the organic layer which separated was removed. The aqueous phase was extracted with ether and the ethereal solution combined with the organic layer and evaporated under diminished pressure to yield 122.8 grams of a mixture of 20% of 2,4-dibutyl-5-propylhexahydropyrimidine and 80% of 5-(2-azaheptyl)-5-propyl-2,4,6-tributylhexahydropyrimidine.

A mixture of 80.5 grams of 20% 2,4-dibutyl-5-propyl-hexahydropyrimidine and 80% of 5-(2-azaheptyl)-5-propyl-2,4,6-tributylhexahydropyrimidine, 150 grams of conc. hydrochloric acid and 150 grams of water was refluxed for 1 hour. The organic phase, 19.1 grams of product, was removed and the acid aqueous solution basified with a sodium hydroxide solution to yield 56.5 grams of a mixture of 20% of 5-amino-4-(aminomethylene) nonane and 80% of 9-amino-8(1-aminopentyl)-8-propyl-6-azatridecane which was separated by distillation:

5-Amino-4(aminomethylene) nonane: b.p. 64°–68° C./0.05 torr, $^{13}C$ nuclear magnetic resonance spectrum, solvent $CDCl_3$, internal reference tetramethylsilane, δ in ppm:

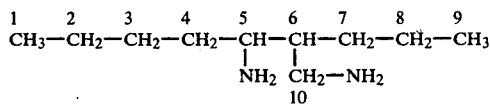

14.1(1); 23.0(2); 29.1(3); 35.2(4); 52.6(5); 46.2(6); 31.3(7); 20.9(8); 14.5(9); 42.0(10).

Calculated for $C_{10}H_{24}N_2$: C, 69.77; H, 13.95; Found: C, 69.59; H, 14.12.

9-Amino-8(1-aminopentyl)-8-propyl-6-azatridecane: b.p. 135°–140° C./0.05 torr, $^{13}C$ nuclear magnetic resonance spectrum, solvent $CDCl_3$, internal reference tetramethylsilane, δ in ppm:

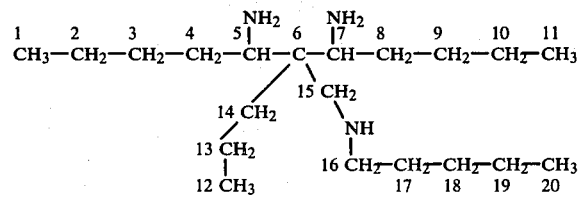

14.2(1,11,20); 23.1(2,10); 29.8(3,9); 32.9 and 37.0(4,8); 56.2 and 55.7(5,7); 44.7(6); 15.6(12); 18.1(13); 32.6(14); 55.3(15); 51.0(16); 29.9(7); 30.2(18); 22.7(19).

Anal. Calc'ed for $C_{20}H_{45}N_3$: C, 73.40; H, 13.76; N, 12.84; Found: C, 73.28; H, 14.10; N, 12.80.

Both the hexahydropyrimides and polyamines such as diamines and triamines of this invention are useful as corrosion inhibitors, fuel additives, biocides, etc. For example, the products described in examples 3, 4 and 5 are particularly effective as corrosion inhibitors, while the products of examples 1 and 3 are useful as biocides. The products described in examples 3 and 5 are useful as fuel additives. Furthermore the reaction products of examples 1, 2, 3 and 4 in combination with fatty acid make excellent corrosion inhibitors.

I claim:

1. A composition selected from the group consisting of compounds of the formula

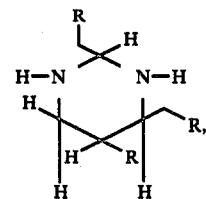

those of the formula

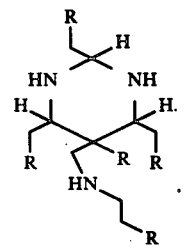

and mixtures thereof, where R is alkyl or aralkyl.

2. A composition of claim 1 which is a compound of the formula

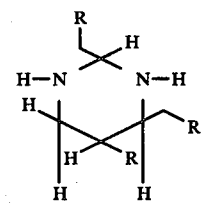

where R is alkyl or aralkyl.

3. A compound of claim 2 wherein R is lower alkyl.

4. A compound of claim 3 which is 2,4-dipropyl-5-ethylhexahydropyrimidine.

5. A composition of claim 1 which is a compound of the formula

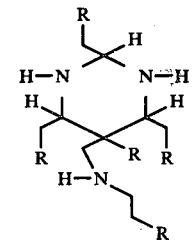

where R is alkyl or aralkyl.

6. A compound of claim 5 wherein R is lower alkyl.

7. A compound of claim 6 which is 5-(2-azapentyl)-5-methyl-2,4,6-triethylhexahydropyrimidine.

8. A compound of claim 6 which is 5-(2-azahexyl)-5-ethyl-2,4,6-tripropylhexahydropyrimidine.

9. A composition of claim 1 which is a mixture of a compound of the formula with a compound of the formula
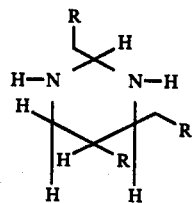
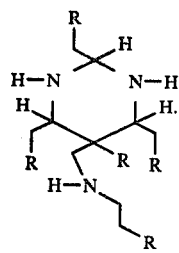
10. A composition of claim 9 wherein R is lower alkyl.
11. A composition of claim 10 wherein the compounds are 2,4-dipropyl-5-ethylhexahydropyrimidine and 5-(2-azahexyl)-5-ethyl-2,4,6-tripropylhexahydropyrimidine, respectively.
* * * * *